United States Patent
Epstein

Patent Number: 5,660,205
Date of Patent: Aug. 26, 1997

[54] ONE-WAY VALVE

[76] Inventor: Alan B. Epstein, 18204 Los Alimos St., Northridge, Calif. 91326

[21] Appl. No.: 356,670

[22] Filed: Dec. 15, 1994

[51] Int. Cl.⁶ ............................................. F16K 15/14
[52] U.S. Cl. ...................... 137/512.15; 137/853; 604/247
[58] Field of Search ............................. 137/1, 512.15, 137/853, 854; 604/247

[56] References Cited

U.S. PATENT DOCUMENTS

| | | | |
|---|---|---|---|
| 1,800,066 | 4/1931 | Glass | 137/853 X |
| 3,384,113 | 5/1968 | Pennisi | 137/853 |
| 3,542,026 | 11/1970 | Bledsoe . | |
| 3,601,151 | 8/1971 | Winnard . | |
| 3,699,961 | 10/1972 | Szpur . | |
| 3,788,327 | 1/1974 | Donowitz et al. . | |
| 4,020,831 | 5/1977 | Adler . | |
| 4,063,555 | 12/1977 | Ulinder | 137/853 X |
| 4,084,606 | 4/1978 | Mittleman . | |
| 4,112,924 | 9/1978 | Ferrara et al. . | |
| 4,346,704 | 8/1982 | Kulle | 604/247 |
| 4,412,836 | 11/1983 | Brignola . | |
| 4,585,209 | 4/1986 | Aine et al. . | |
| 4,759,752 | 7/1988 | Stober | 137/853 X |
| 4,819,684 | 4/1989 | Zaugg | 137/853 X |
| 4,832,054 | 5/1989 | Bark . | |
| 4,850,393 | 7/1989 | Lashomb . | |
| 4,919,167 | 4/1990 | Manska . | |

*Primary Examiner*—John Rivell
*Attorney, Agent, or Firm*—Blakely, Sokoloff, Taylor & Zafman

[57] ABSTRACT

A method and apparatus is disclosed for supplying a fluid under pressure to a channel and for blocking a backflow of fluid from the channel to a catheter. The apparatus is a one-way valve assembly for use with a container supplying a fluid under pressure to a channel. The one-way valve assembly includes a first tube for communicating the fluid into a channel, a valve, and a second tube communicating with the container supplying the fluid and transmitting the fluid to the first tube via the valve. The valve comprises a base member with a hollow interior and a sealed distal end, which hollow interior is capable to communicate the fluid between the second tube and the first tube through at least one slit aperture which is positioned near the sealed distal end of the base member. The base member is engaged and covered by a flexible pressure-responsive surface which seals the slit aperture in order to prevent backflow of fluid from the first tube into the base. The flexible pressure-responsive surface, however, unseals the slit aperture to permit forward flow of the fluid.

15 Claims, 1 Drawing Sheet

ONE-WAY VALVE

BACKGROUND OF THE INVENTION

1. Field of the Invention

The present invention relates to a one-way valve for use with a medical device where it is desired to transfer fluid from a fluid source to a medical device or patent. More specifically, this invention is directed to prevent the backflow of blood or other medical fluid and to prevent the occurrence of excessively rapid flow infusion.

2. Art Background

The intravenous infusion of medical fluids in patients has long been recognized to be useful. However, certain problems related to intravenous infusions have persisted over the years.

A typical problem associated with intravenous infusion is the reverse flow of fluid into a cannula, such as a catheter tube or IV or IA needle that is inserted typically into a patient's vein or artery. For example, during the delivery of a solution to a patient through a cannula, one cannot predict accurately when the supply of IV solution become exhausted if the flow of the IV solution is generated by gravity. While this problem can be remedied by using a infusion pump which can be timed or by setting alarms to alert the personnel when an IV solution becomes exhausted, one still needs to solve the problem related to the difficulty in coordinating the availability of nursing personnel for disconnecting, at the right time, the soon-to-be-exhausted IV supply from the catheter tube or needle that is infused in the patient. Even where the supply of IV fluid does not become exhausted, the patient may raise the venipuncture location above the IV fluid source, thus, causing a reverse flow of fluid into the cannula (venipuncture meaning the place in the patient's vein or artery where a first tube is inserted). As a consequence of the problems enumerated above, the distal part of the cannula is affected by bleedback, and clotting in the cannula may result.

In a standard IV dispensing system where a fluid source is attached to the proximal end of a cannula, the flow of IV fluid into the cardiovascular system of the patient occurs because gravity exerts a force upon the IV fluid which exceeds the blood pressure in the cardiovascular system of the patient. When the IV fluid to be infused into the patient is low or exhausted, the difference between the IV fluid pressure and the patient's blood pressure, which initially drove the fluid down the cannula to the patient, changes so that the cardiovascular pressure prevails, giving rise to a blood backflow into the IV cannula. This backflow of blood contaminates the cannula such that within a short time, a clot may be formed in the cannula. As a consequence, an unacceptable risk arises that a clot may be introduced into the blood stream of the patient. It then becomes necessary to replace the catheter adding additional risk and expense to the medical care of the patient.

Several suggestions have been proposed to resolve the above-mentioned problem. Among these approaches, the closest to the present invention is a one-way outdwelling (outside the body of a patient) standard valve which prevents undesired blood flow into the distal end of an indwelling cannula. These approaches, however, do not have the advantages provided by the present invention.

For example, one such approach close to the present invention is an apparatus designed to prevent backflow due to pressure differentials. The "Nonreturn valve for medical uses," disclosed in the U.S. Pat. No. 3,601,151, issued to Winnard, discloses a one-way valve which, in one embodiment, is coupled between a needle inserted into a vein and a syringe used to withdraw blood samples. The valve member includes a body defining a void path through the valve, a bored stem constituting part of the path, and a chamber in which the stem is located and which is also part of the path. The stem portion is provided with a bore so that fluid passes into the chamber and through the valve. The stem part acts as a seat for the valve-closure member, which is an elastic sock which opens by expansion under the pressure exerted from the stem side of the valve. The elastic sock has a closed end about an inlet orifice of the stem, so that liquid must pass about the inner surface of the elastic sock closed end, and then move rearwardly about the orifice until the inner end of the sock is passed. The fluid then turns 180° and flows along the outer surface of the sock outwardly on its path to the catheter. The valve is closed when the pressure is removed and the sock contracts under its own elasticity around the stem. In its neutral configuration, thus, the elasticity of the sock member seats the sock on the cylindrical surface of the stem, thereby preventing fluid flow through the stem. Reverse pressure forces the sock against the cylindrical surface, preventing flow in the reverse direction.

The disadvantage of the Winnard apparatus is that if the reverse pressure is high, the sock member may be subject to rupture. If a more resistant sock is provided, however, the valve will display less sensitivity to pressure differentials. Because the sock and stem might be specially sized for each particular bursting pressure, this type of valve is expensive to manufacture where valves of different bursting pressures are desired. Furthermore, this closed-end sleeve structure can shift and block an outlet orifice, possibly rendering the valve inoperative.

Bledsoe, U.S. Pat. No. 3,542,026, discloses a thoracostomy device to remove air and fluid from the area of the lungs through an elastic bulb having an air chamber connected by a tube to the pleural cavity to draw fluid from the cavity through the tube into the chamber of the bulb. At the inlet end of the bulb, a one-way valve is provided which closes the end of the tube as the fluid is discharged from the opposite end of the bulb. The Bledsoe device does not transport liquid, but only air.

Aine, et al., U.S. Pat. No. 4,858,209, discloses a miniature valve having the cantilever leaf spring disposed overlying an apertured plate for controlling the flow of fluid therethrough. An electrostatic potential applied between the cantilever leaf spring and the valve plate pulls the leaf spring over the apertured plate for variably controlling flow through the valve in accordance with the magnitude of the applied potential. Aine, et al.'s device uses an electrical current to open and close the valve.

Lashomb, U.S. Pat. No. 4,850,393, discloses an all-plastic check valve for a molded plastic surgical or medical device. A hollow cone-shaped or bullet-shaped stopper permits fluid flow in one direction, but in the back direction lodges against the ceiling ring or seat. The Lashomb device is structured differently and functions differently than the present invention.

Mittleman, U.S. Pat. No. 4,084,606, involves multiple sources of fluid and multiple paths of flow.

Mansca, '167, Adler, '831, Mittleman, '606, and Donowitz, et al., '327 patents disclose alternate flap valve configurations, while Szpur, '961, Ferrara, et al., '924, Brignola, '836, and Bark, '054 patents disclose other types of mechanical one-way valves that are not related to the configuration or design of the present invention.

There is a need, thus, for a better method and apparatus for preventing the backflow of blood into an intravenous or intra-arterial cannula and to prevent the occurrence of excessively rapid flow infusion which apparatus and method do not have the drawbacks of the prior art.

SUMMARY OF THE INVENTION

A method and apparatus are disclosed which overcome the disadvantages and limitations associated with prior art one-way valves designed to prevent the backflow of blood into intravenous or intra-arterial cannula and to prevent the occurrence of excessively rapid flow infusion.

It is an object of the present invention to provide a method and an apparatus for dispensing a medical fluid from a fluid container to a channel avoiding the backflow of fluid into a cannula when the pressure in the fluid container falls below a predetermined value.

It is also an object of the present invention to provide a method and an apparatus which would reduce or eliminate the need to replace the elastic members of valves, like the one patented by Winnard, which elastic members are ruptured by high reverse pressures. The present invention overcomes this limitation of the prior art.

It is a further object of the present invention to provide a method and apparatus for preventing the backflow of fluid in a fluid-dispensing medical device utilizing a one-way valve assembly when only slight differences in the pressure gradient on either side of the valve are present. Thus, the present invention provides for a method and apparatus which will enable the prevention of backflow of blood, where the apparatus and the method display a high sensitivity to pressure differentials.

It is also an object of the present invention to provide a one-way valve which prevents the backflow of fluid, yet allowing various flow rates to be maintained up to a limit. However, the valve of the present invention does not hinder rapid intentional injection of medication.

It is further another object of the present invention to provide one-way valve assemblies which are capable of withstanding a wide range of pressures, so that the need for utilizing a multiplicity of valves adapted to withstand different bursting pressures is eliminated. Thus, the present invention provides for an inexpensive and versatile way of dispensing fluids to a channel avoiding the backflow of blood into an intra-arterial or intravenous cannula.

This and other objects of the present invention are provided in a method and apparatus for dispensing a fluid to a patient's arteries or veins without allowing the blood to flow back into the catheter.

The present invention preferably consists of a one-way valve assembly accommodating flow of fluid, but not limited to, flow of IV fluid through a first tube which could be, but is not limited to, a cannula, transmitting a flow of fluid to a channel which could be, but is not limited to, the cardiovascular system of a patient. The assembly utilizes a novel one-way valve controlling the flow of the fluid to the cannula, and a second tube, which can be, but is not limited to, a drip tube which transmits a fluid maintained under a certain pressure in a container which can be, but is not limited to, an IV vial.

In one presently preferred manifestation of the present invention, the one-way valve comprises a base member and a flexible pressure-responsive surface. The base member has a hollow interior and a sealed distal end. The proximal end of the base member is open, allowing fluid communication with a second tube connected to a container. The distal end of the base member, being sealed, does not allow fluid to be passed directly through this end. Instead, the fluid may flow through at least one slit aperture which can be found on the sides of the base member. The slit aperture can be provided by making several thin slit cuts into the sides of the base near its distal end. Further, in one preferred embodiment, the base is engaged with a flexible pressure-responsive surface, which can be, but is not limited to, an elastomeric sheath which ensures that the slit aperture is tightly sealed. The sealing of the slit aperture is effected by the natural resilience of the flexible pressure-responsive surface which contracts under its own elasticity around the distal part of the base on which the aperture is disposed. When the pressure in the container drops below a predetermined value, which can be equal to the pressure in the first tube, which pressure can be, but is not limited to, the blood pressure of the patient upon which the infusion is performed, the slit apertures remain sealed. However, when the pressure induced in the container exceeds a predetermined value, which could be equal to the first predetermined value, the elastomeric sheath can separate from the slit aperture of the base, allowing the fluid to flow through this aperture into the first tube and further into the channel to be infused.

Stated another way, the present invention provides a pressure-responsive valve that opens in response to the higher pressure exerted by a full IV solution container or bottle, but closes as the pressure drops, as the container or bottle empties, solving or greatly reducing the problem of replacing the elastomeric sheath which would otherwise need to be replaced due to ruptures resulting from prior art one-way valves like the valve patented by Winnard.

These and other objects and features of the present invention will be apparent from the detailed description taken with reference to the accompanying drawings.

DETAILED DESCRIPTION OF THE INVENTION

A method and apparatus are described which are used in dispensing a fluid to a channel, which can be, but is not limited to, an artery or a vein. The preferred embodiment of the present invention might be best described as an apparatus and a method for dispensing a medical fluid into the intravenous or intra-arterial system of a patient such that the back flow of blood to a catheter is prevented by a one-way valve of the present invention. It should be borne in mind that the present invention need not be limited in use for intravenous or intra-arterial infusion, but may find wide application for the infusion of any channels. Also, the medical fluid which is dispensed can be replaced by any other fluid.

In reference to the detailed description of the invention which follows, the following definition of terms used in the description of the invention and also in the claims may be useful in understanding the invention. It should be borne in mind, however, that all of these definitions are by no way limiting, but they are only a way of explaining the terms used in the description of the invention. Flex opens means elastically separating from a surface. The word container, by way of example, can be any IV or IA fluid bottle or vial. The word channel is referring to any vein, artery or, more generally, any channel, which can be found in a patient's body or channel, in general. The word first tube can be a tubular structure used for transferring fluid. By way of example, the first tube can be a cannula or, more specifically, a catheter which can be inserted into a patient's blood vessels. The second tube can be a tubular structure which can be used to communicate fluid from an IV bottle, and more specifically, can be a drip line.

As described herein, the terms "distal" or "distal end" are intended to refer to the surface or portion of a member or element closest to the sealed end of the base member 16 in the valve assembly 10 as described hereinafter. The terms "proximal" or "proximal end" are intended to define the surface or portion of a member or element which is located furthest from the sealed end in the valve assembly 10 as described hereinafter.

With regard to slit aperture, slit aperture can be any thin slit in the base which allows communication between an interior part or surface of the body in which the slit aperture is made and the outer part or surface of the respective body. With respect to flexible pressure-responsive surface, it can be any surface or sheath made of soft, elastomeric material that responds to pressure by stretching away from the body with which this sheath is engaging, and that regains its shape, typically, but not necessarily, contracting under its own elasticity, when the pressure or force which was acting upon it has been removed.

Figure 1:
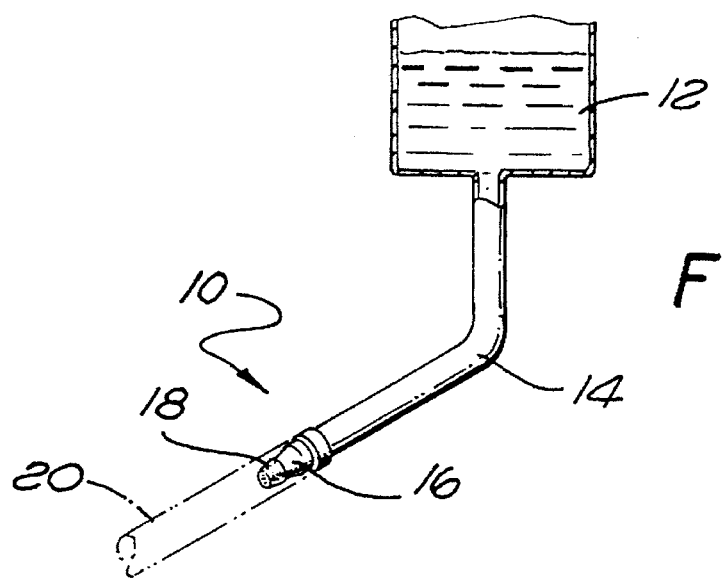
FIG. 1 is a perspective illustration of a one-way valve assembly of the present invention.

FIG. 1 shows one embodiment of a medical fluid-dispensing assembly of the present invention. With reference to this figure, the valve according to the present invention is a one-way valve. The one-way valve, according to the present invention, as illustrated in FIG. 1, is used in conjunction with a fluid bottle, purely by way of example, the valve being capable for use with other types of containers without any modification. The fluid-dispensing valve-assembly of the present embodiment is designated herein generally as valve assembly 10.

As illustrated in FIG. 1, the valve assembly 10 preferably consists of a container 12 supplying a fluid under pressure, where the container 12 is suspended at a height above the venipuncture sight (not shown). The container 12, containing the fluid to be dispensed to a channel, which channel is not shown in FIG. 1, generates a pressure in the container, which pressure causes the fluid from the container to be infused into the second tube 14, to a one-way valve consisting of a base 16 and a flexible pressure-responsive surface 18, and from the one-way valve to the second tube 20, shown in ghost lines, which further transmits the fluid to the channel. Also, while FIG. 1 shows, by way of example, the fluid bottle 12 which contains the fluid to be infused and also creates a pressure upon this fluid, by means of gravitation, the present embodiment does not limit in any way the disclosed invention. The fluid bottle 12 can be replaced by any infusion device including IV vials or other containers. The fluid in the container 12 can be actuated or driven by other forces such as, for example, manual compression or automatic compression.

Figure 2:
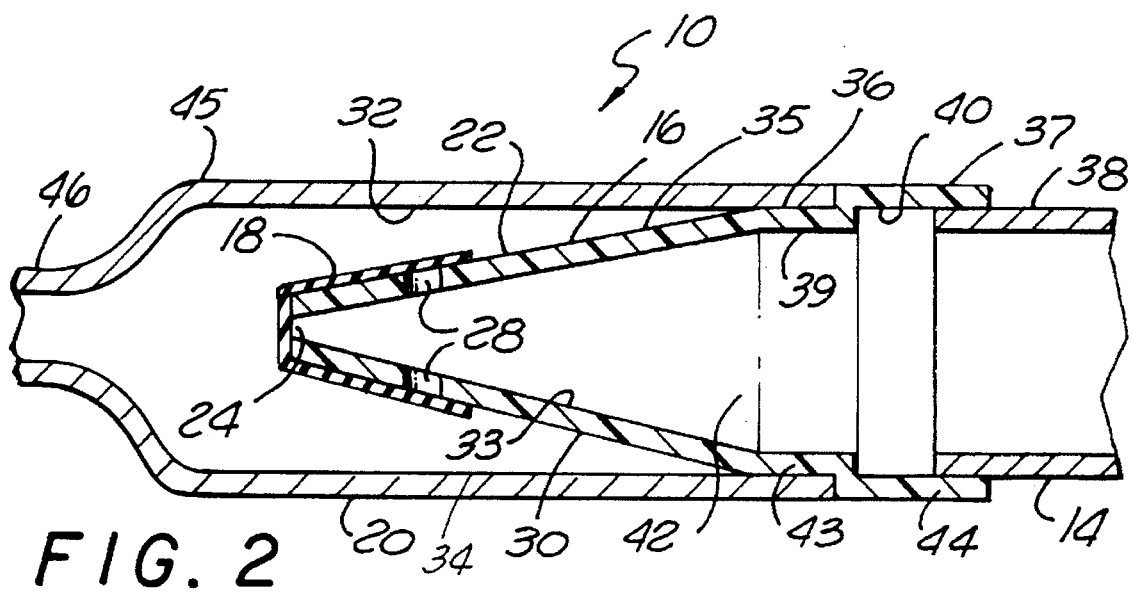
FIG. 2 is an enlarged sectional view of the one-way valve assembly of FIG. 1, the assembly being in a position where the flow of fluid from the base to the first tube is prevented.

Referring now to FIG. 2, the second tube 14 communicates fluids with the base member 16 through a hollow interior 42. The hollow interior 42 of the base 16 also serves as a medium for communicating the fluid between the second tube 14 and the first tube 20. In the embodiment shown in FIG. 2, the base member 16 consists of a trunconical member 30, a first cylindrical member 43 abutting the trunconical member at a proximal end thereof and a second cylindrical member 44 constituting the proximal part of the base 16, abutting the cylindrical member 43 at a proximal end thereof. Furthermore, the outer surface 35 of the trunconical member 30 is contiguous with the outer surface 36 of the first cylindrical member and the outer surface 37 of the second cylindrical member 44. The inner surface 33 of the trunconical member 30 is contiguous with an inner surface 39 of the first cylindrical member 43 and the inner surface 40 of the second cylindrical member 44 such that the trunconical member 30 and the first cylindrical member 43 and the second cylindrical member 44 constitute one single body.

The second tube 14 has an outer surface 38, frictionally engaged with a proximal part of an inner surface 40 of the second cylindrical member 44. The engagement between the second tube 14 and the base 16 provides a fluid-tight seal such that the fluid communicated from the fluid container 12 to the base 16 through the second tube 14 will not escape through the proximal end of the base. Further, outer surface 36 of the first cylindrical member 43 is frictionally engaged with the interior surface 32 of the first tube 20. This frictional engagement creates a fluid-tight seal between the outer surface 36 and the interior surface 32 of the first tube 20 so that fluid cannot escape between surface 32 and surface 36 through the proximal end of the base.

The base 16 can be made of a firm plastic or another alternate firm body. The second tube 14 has a generally cylindrical configuration and can be a drip line. This tube can be made of different flexible materials.

The trunconical member 30 has a truncated conical shape having at its distal end a flatly sealed tip 24 of circular shape. The embodiment illustrated in this figure, by no means limits the claimed invention. Instead of the trunconical shape of the member 30, the present invention could be implemented with a body of a different shape, like for instance a semi-spherical shape.

In the trunconical member 30, FIG. 2 displays a slit aperture 28. In the present invention, the number of slit apertures 28 is not limited to what is shown in FIG. 2, but rather the number of such apertures can vary. However, to be operative, the invention needs at least one such aperture. However, while the slit apertures 28, as illustrated in FIG. 2, are adjacent to the distal end of the trunconical member 30, these slit apertures can be positioned, in other embodiments of the present invention, anywhere on a side surface 22 of the trunconical member 30, as long as these apertures can be sealed by a flexible pressure-responsive surface 18 which is disposed about the distal tip 24 of the base 16, and as long as these apertures can enable the fluid to flow from the hollow interior of the base through the slit aperture 28 and into the first tube 20. The slit aperture 28 can be a thin slit cut into the body 30. The purpose of the slit aperture 28 is to allow the fluid transmitted by the second tube 14 to flow through the base 16 into the first tube 20.

As shown in FIG. 2, a one-way assembly 10 comprises a second tube 14 connected to a proximal end of the base 16, a first tube 20 connected to the outer surface of the base 16, the hollow base 16 having a sealed distal end 24, and a flexible pressure-responsive surface 18 engaging a distal part of the base and sealing a slit aperture 28 adjacent to the distal end of the base.

FIG. 2 further shows the distal end of the base 16 having a sealed tip 24. The reason for sealing the distal end of the base 16 by the tip 24 is to prevent the flow of fluid from the second tube 14 to the first tube 20 through the tip 24 itself. While in the prior art the communication of fluid between the analogous of the base 16 and the analogous of the first tube 20 was performed through the tip of the base, in a preferred embodiment of the present invention illustrated in FIG. 2, the fluid does not exert a force perpendicularly oriented to the tip, and, thus, the potential rupture of whatever elastic seal would be covering the tip of the base and its sides is greatly diminished.

FIG. 2 further illustrates a flexible pressure-responsive surface 18 disposed about the distal end of the base 16 (which distal end coincides with the distal end of the trunconical member 30) and sealing the slit aperture 28. As illustrated in FIG. 2, the flexible pressure-responsive surface 18 is engaged with the distal end of base 16 and the distal part of the trunconical member 30 due to the resiliency of the surface 18 which contracts under its own elasticity. Preferably, the flexible pressure-responsive surface 18 is otherwise adhered to the trunconical member 30 of the base 16. The surface 18 provides a tight sealing of the slit aperture 28 to prevent a backflow of fluid from the first tube 20 to the base 16 through the slit aperture 28 when the pressure in the base is lower than the pressure in the first tube 20. The flexible pressure responsive surface 18 can be made by dipping the distal part of the base 16 into a polyurethane solution and then curing it to form it into its permanent, soft, elastic form. However, other methods of manufacturing the flexible pressure-responsive surface can be employed which can provide this surface with the same qualities as the ones enumerated in the above-mentioned method. For example, the surface can be formed on a mandrel and then applied to the base as a separate step.

The first tube 20 illustrated in FIG. 2 can be any type of tubular structure that is capable to transport the fluid from the base 16 to the channel (not shown in the drawings). In the preferred embodiment illustrated in FIG. 2, the first tube 20 consists of a larger tubular section 45 and a smaller tubular section 46 where the tubular section 46 has a smaller diameter than the larger tubular section 45. The first tube 20 can be a catheter utilized for entering the arteries or veins of a patient and infusing a fluid into these blood vessels.

Figure 3:
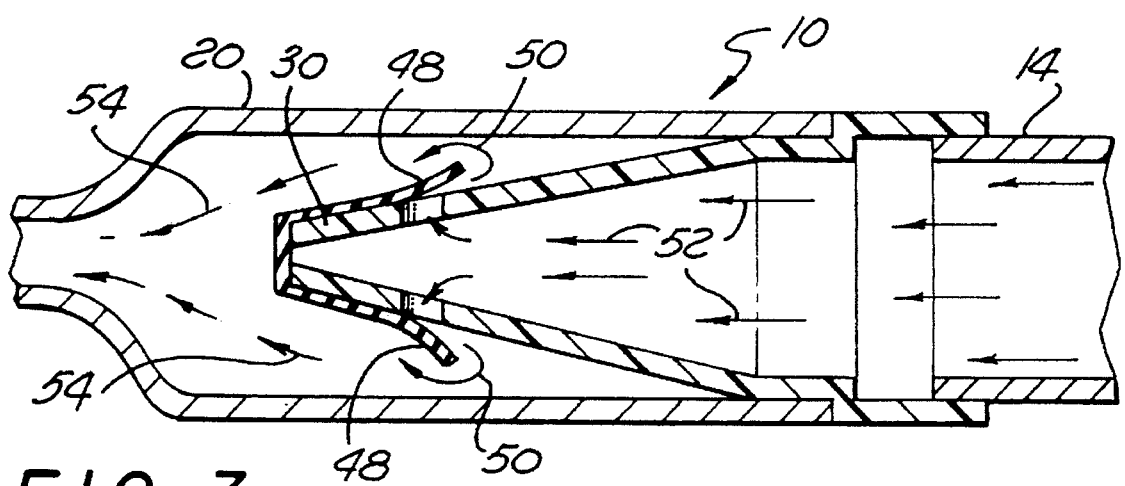
FIG. 3 is a sectional view of the same embodiment of the FIG. 2 where, however, the flexible pressure-responsive surface is separated from the slit aperture and base member allowing a flow of fluid through the base to the catheter.

FIG. 3 shows the valve assembly 10 in use with a fluid passing through the base 16. When the pressure of the fluid contained in the container (not shown) and transported through the second tube 14 exceeds a predetermined value, which is, but is not limited to, the pressure in the first tube 20, the fluid will flow from the second tube 14 to the base 16 in the direction indicated by the arrows 52. The pressure in the container 12 forces the flexible pressure-responsive surface 18 to separate from the slit aperture 28 and the outer side surface 22 of the trunconical member 30 along the area of least resistance. As it is illustrated in FIG. 3, a proximal part 48 of the flexible pressure-responsive surface 18 is separated toward the proximal end of the base 16. The separation of the proximal part 48 of the flexible pressure-responsive surface 18 from the trunconical member 30 unseals the slit aperture 28, thus, allowing the fluid, flowing through the base 16 in the direction indicated by the arrows 52, to flow through the slits 28 rearwardly and then towards the proximal end of the flexible pressure-responsive surface 18 until the fluid passes this proximal end, at which point the fluid is forced to change its direction of flow towards the distal end of the flexible pressure-responsive surface as indicated by the arrows 50. Further, the fluid is forced to flow as indicated by the arrows 54 towards the proximal end of the first tube 20.

A screen may be placed on the venous (arterial) side of the valve as a safety precaution against the unlikely event of the valve material dislodging and entering the channel (not shown).

With this one way valve, any necessary flow rate can be maintained using a mechanical infusion device, up to the limit of the strength of the flexible pressure responsive surface. If gravity is used as the driving force of the fluid, flow rates up to 120 milliliters per hour can be obtained. This also means that the problem of runaway infusion is virtually eliminated by use of this valve. However, rapid (intentional) injection of medication is not hindered by the valve.

While the method and apparatus have been described in terms of various embodiments, other embodiments may come to mind to those skilled in the art without departing from the spirit and scope of the present invention. The invention should, therefore, be measured in terms of the claims which follow.

What is claimed is:

1. In a one-way valve assembly for use with a container supplying a fluid under a pressure to a channel, said one-way valve assembly including a first tube for communicating said fluid into said channel, a valve, and a second tube communicating with said container and transmitting said fluid to said first tube via said valve, said valve comprising:

a base member having a hollow interior and a sealed distal end, said hollow interior being capable of communicating said fluid between said first tube and said second tube through at least one aperture adjacent to said sealed distal end;

a flexible pressure-responsive surface comprising a sheath of a soft elastomeric material covering said at least one aperture, said flexible pressure responsive surface elastically engaged to said sealed distal end of the base member, thereby sealing said aperture to prevent a flow of fluid from said first tube into said base member when said pressure falls below a predetermined value, and remaining elastically engaged to said sealed distal end of the base member but stretching away from said aperture to unseal said aperture when said pressure exceeds the predetermined value.

2. The one-way valve assembly of claim 1 wherein said first tube is a catheter.

3. The one-way valve assembly of claim 1 wherein said second tube is a drip tube.

4. The one-way valve assembly of claim 1 wherein said channel is a blood vessel.

5. The one-way valve assembly of claim 1 wherein said flexible pressure-responsive surface is fabricated by dipping a distal part of the base member into an elastomeric emulsion and subsequently curing it.

6. The one-way valve assembly of claim 5 wherein said elastomeric emulsion is polyurethane.

7. The one-way valve assembly of claim 1 wherein said fluid can attain a flow rate of up to 120 milliliters per hour, if said pressure under which said fluid is supplied by said container is generated by subjecting said container to a force of gravity.

8. The one-way valve assembly of claim 1 wherein said pressure is generated by a mechanical infusion device.

9. In a one-way valve assembly for use with a container supplying a fluid under a pressure to a channel, said one-way valve assembly including a first tube for communicating said fluid into said channel, a valve, and a second tube communicating with said container and transmitting said fluid to said first tube via said valve, said valve comprising:

a base member having a hollow interior and a sealed distal end, said hollow interior being capable of communicating said fluid between said first tube and said second tube through at least one slit aperture adjacent to said sealed distal end;

a flexible pressure-responsive surface covering said at least one slit aperture, said flexible pressure responsive surface engaging with said base member, thereby sealing said slit aperture to prevent a flow of fluid from said first tube into said base member when said pressure falls below a predetermined value, and unsealing said slit aperture when said pressure exceeds the predetermined value wherein said base member comprises a distal trunconical part having a tip and a side surface, a second cylindrical part located at a proximal end of said base, and a first cylindrical part connecting said distal trunconical part with said second cylindrical part, said slit aperture being disposed on said side surface, said first cylindrical part having an outer surface capable of frictionally engaging an inner proximal part of said first tube, said second cylindrical part having an inner surface capable of frictionally engaging an outer surface of said second tube at a distal end thereof.

10. In a one-way valve assembly for use with a container supplying a fluid under a pressure to a blood vessel, said medical fluid infusion assembly including a first tube for communicating said fitted into said blood vessel, a one-way valve, and a second tube communicating with said container and transmitting said fluid to said first tube via said one-way valve, said one-way valve comprising:

a base member capable of communicating said fluid between said first and second tube, wherein said base member is constituted by a distal trunconical part having a tip and a side surface, a second cylindrical part located at a proximal end of said base, and a first cylindrical part connecting said distal trunconical part with said second cylindrical part, a slit aperture being disposed on said side surface, said first cylindrical part having an outer surface capable of frictionally engaging an inner proximal part of said first tube, said second cylindrical part having an inner surface capable of frictionally engaging an outer surface of said second tube at a distal end thereof;

a flexible pressure-responsive surface covering said at least one slit aperture, said flexible pressure responsive surface engaging with said base member, thereby sealing said slit aperture to prevent a flow of fluid from said first tube into said base member when said pressure falls below a predetermined value, and unsealing said slit aperture when said pressure exceeds the predetermined value.

11. The one-way valve assembly of claim 10 wherein said second tube is a drip tube.

12. The one-way valve assembly of claim 10 wherein said flexible pressure-responsive surface is fabricated by dipping said distal end into an elastomeric emulsion and subsequently curing it.

13. The one-way valve assembly of claim 12 wherein said elastomeric emulsion is polyurethane.

14. The one-way valve assembly of claim 10 wherein said fluid can attain a flow rate of up to 120 milliliters per hour, if said pressure under which said fluid is supplied by said container is generated by subjecting said container to a force of gravity.

15. The one-way valve assembly of claim 10 wherein said pressure is generated by a mechanical infusion device.

* * * * *

UNITED STATES PATENT AND TRADEMARK OFFICE
CERTIFICATE OF CORRECTION

PATENT NO. : 5,660,205
DATED : August 26, 1997
INVENTOR(S) : Epstein It is certified that error appears in the above-identified patent and that said Letters Patent is hereby corrected as shown below:

In column 1 at line 21, please delete " a " and insert -- IV --. (1st occurrence)

In column 1 at line 22, please delete " solution " and insert -- solution will --.

In column 3 at line 12, please delete " cannual " and insert -- cannulae --.

In column 9, claim 10 at line 29, please delete " fitted " and insert -- fluid --.

Signed and Sealed this

Eighth Day of December, 1998

*Attest:*

BRUCE LEHMAN

*Attesting Officer*   *Commissioner of Patents and Trademarks*